(12) United States Patent
Kadkhodayan et al.

(10) Patent No.: US 7,732,390 B2
(45) Date of Patent: Jun. 8, 2010

(54) PHENOLIC DIMERS, THE PROCESS OF PREPARING SAME AND THE USE THEREOF

(75) Inventors: Abbas Kadkhodayan, Collinsville, IL (US); Ju-Fu Shiau, Chesterfield, MO (US); Joe S. Bradley, Midlothian, VA (US); Cathy C. Devlin, Richmond, VA (US); Charles A. Passut, Midlothian, VA (US)

(73) Assignee: Afton Chemical Corporation, Richmond, VA (US)

( * ) Notice: Subject to any disclaimer, the term of this patent is extended or adjusted under 35 U.S.C. 154(b) by 1588 days.

(21) Appl. No.: 10/995,097

(22) Filed: Nov. 24, 2004

(65) Prior Publication Data

US 2006/0111257 A1 May 25, 2006

(51) Int. Cl.
*C10L 1/22* (2006.01)
(52) U.S. Cl. ..................... 508/542; 508/287
(58) Field of Classification Search .......... 508/287
See application file for complete search history.

(56) References Cited

U.S. PATENT DOCUMENTS

| | | | |
|---|---|---|---|
| 2,675,366 A | 4/1954 | Pullman | |
| 3,238,263 A | 3/1966 | Schetelich et al. | |
| 3,372,116 A | 3/1968 | Meinhardt | |
| 3,657,133 A | 4/1972 | Miller | |
| 4,087,469 A | 5/1978 | Gurvich et al. | |
| 4,800,032 A | 1/1989 | Murphy | |
| 5,082,470 A | 1/1992 | Martella et al. | |
| 5,102,566 A | 4/1992 | Fetterman, Jr. et al. | |
| 5,114,601 A | 5/1992 | Cook et al. | |
| 5,162,085 A | 11/1992 | Cane et al. | |
| 5,205,946 A | 4/1993 | Cook et al. | |
| 5,330,665 A | 7/1994 | Cane et al. | |
| 5,366,648 A | 11/1994 | Salomon et al. | |
| 5,569,405 A | 10/1996 | Nakazato et al. | |
| 5,629,272 A | 5/1997 | Nakazato et al. | |
| 6,002,051 A | 12/1999 | Burjes et al. | |
| 6,103,672 A | 8/2000 | Dunn et al. | |
| 6,248,142 B1 | 6/2001 | Caprotti | |
| 6,310,009 B1 * | 10/2001 | Kocsis et al. | 508/186 |
| 6,331,510 B1 | 12/2001 | Curtis et al. | |
| 6,455,477 B1 | 9/2002 | L'Heureux | |
| 6,559,105 B2 | 5/2003 | Abraham et al. | |
| 6,569,818 B2 | 5/2003 | Nakazato et al. | |
| 6,593,281 B2 | 7/2003 | Sato et al. | |
| 6,610,637 B2 | 8/2003 | Curtis et al. | |
| 6,649,575 B2 | 11/2003 | Robson | |
| 6,673,751 B1 | 1/2004 | Cressey et al. | |
| 6,720,293 B2 | 4/2004 | Bovington et al. | |
| 6,764,982 B2 | 7/2004 | Bardasz et al. | |
| 6,784,143 B2 | 8/2004 | Locke et al. | |
| 6,803,350 B2 | 10/2004 | Lantuejoul et al. | |
| 6,809,069 B2 | 10/2004 | Deshimaru et al. | |
| 2001/0036906 A1 | 11/2001 | Locke et al. | |
| 2004/0102335 A1 | 5/2004 | Carrick et al. | |

FOREIGN PATENT DOCUMENTS

| | | |
|---|---|---|
| EP | 0 450 874 A2 | 10/1991 |
| EP | 0 450 874 A3 | 10/1991 |
| JP | SHO/51-34989 | 3/1976 |
| JP | SHO/60-80848 | 5/1985 |
| JP | HEI/4-505637 | 10/1992 |
| JP | HEI/6-80563 | 3/1994 |
| RU | 2172752 C2 * | 8/2001 |

OTHER PUBLICATIONS

Pivcova, H. et al., Antioxidants and stabilizers. XLIII. Structure of phenolic antioxidants and infrared sprectra of the hydroxyl groups, Journal of Polymer Science, Polymer Symposia, 1973. No. 40, pp. 283-295.
Prusikova, M. et al., Antioxidants and stabilizers. XXVI. Influence of the structure of methylene bisphenols on their antioxidative activity in tetralin, Erdoel und Kohle, Erdgas, Petrochemie vereinigt mit Brennstoff Chemie, 1972, vol. 25, No. 2, pp. 80-83.

* cited by examiner

*Primary Examiner*—Glenn A Caldarola
*Assistant Examiner*—Taiwo Oladapo
(74) *Attorney, Agent, or Firm*—Mannava & Kang, PC

(57) ABSTRACT

This invention relates to detergents, lubricating oil additives and compositions, and methods of preparing detergents, lubricating oil additives and compositions. More specifically, this invention relates to novel phenolic dimers.

37 Claims, No Drawings

PHENOLIC DIMERS, THE PROCESS OF PREPARING SAME AND THE USE THEREOF

BACKGROUND OF THE INVENTION

1. Field of the Invention

This invention relates to detergents, lubricating oil additives and compositions, and methods of preparing detergents, lubricating oil additives and compositions. More specifically, this invention relates to novel phenolic dimers.

2. Background Art

Lubricating oil compositions, as used in the internal combustion engines and transmissions of automobiles or trucks, are subjected to a demanding environment. This environment results in the lubricating oil composition suffering oxidation that is catalyzed by the presence of impurities in the lubricating oil composition, such as iron compounds. Additionally, oxidation of the lubricating oil composition is promoted by the elevated temperatures of the lubricating oil composition during use.

The oxidation of the lubricating oil composition during use is usually controlled to some extent by the use of additives, such as antioxidants or acid neutralizers, which may extend the useful life of the lubricating oil composition, particularly by reducing or preventing unacceptable viscosity increases.

One class of antioxidants and acid neutralizers generally employed in lubricating oils are metal alkyl phenates. The metal of the metal alkyl phenates is generally an alkaline earth metal such as calcium, magnesium, or barium.

Examples of metal alkyl phenates are found in U.S. Pat. Nos. 5,330,665 and 5,162,085. The metal alkyl phenates disclosed in these patents are overbased, monomeric, alkyl phenols.

In recent years, phosphorus compounds and sulfur (from sulfonates, sulfur-containing phenates, and metal-containing dithiophosphates) derived from engine lubricants have been shown to contribute in part to particulate emissions. Also, sulfur and phosphorus tend to poison the catalysts used in catalytic converters, resulting in a reduction in performance of the catalysts.

U.S. Pat. No. 6,310,009 B1 and U.S. Publication No. 2004/0102335 A1 describe the use of an overbased saligenin derivative additive in lubricating oil compositions to reduce engine wear and corrosion that is capable of decreasing sulfur and phosphorus containing emissions.

A need exists in the art for improved additives that act to control viscosity, neutralize acid, and/or reduce oxidation. The novel phenolic dimer and the overbased phenolic dimer detergent of the present invention provide anti-wear benefit to lubricating oil compositions with a low phosphorus content and a low sulfur content.

BRIEF SUMMARY OF THE INVENTION

In one aspect, the disclosure herein is directed to novel phenolic dimers that contain a long chain hydrocarbyl group in the para position of each of the two phenols and either an alkyl or alkenyl group in one of the ortho positions of each phenol. The two substituted phenols are linked by an alkylene group in the other ortho position of each phenolic molecule. Additionally, the present disclosure is directed to a method of synthesizing the novel phenolic dimers.

In another aspect, there is presented herein a method of overbasing the phenolic dimers.

In still another aspect, the disclosure herein is directed to novel overbased phenolic dimers that function as an antioxidant in a lubricating oil composition.

In yet another aspect, the disclosure herein is directed to a lubricating oil composition or a lubricating oil concentrate containing the novel overbased dimers.

In still yet another aspect, there is presented herein a method of lubricating an internal combustion engine with the lubricating oil composition containing the novel overbased dimers.

DETAILED DESCRIPTION OF THE INVENTION

The present disclosure is directed to novel phenolic dimers, compositions resulting from overbasing these dimers with an alkaline earth metal source, and the use these dimers as an antioxidant in a lubricating oil composition or a lubricating oil concentrate.

The term "overbased" is used to describe alkaline earth metal alkyl salts of phenolic molecules, phenates, in which the ratio of the number of equivalents of the alkaline earth metal moiety to the number of equivalents of the phenol moiety is greater than one. The ratio is usually greater than 1.2, but may be greater than 4.5. In comparison, the equivalent ratio of alkaline earth metal moiety to phenol moiety in conventional alkaline earth metal phenates is one to one.

The term "TBN" as employed herein is used to denote the Total Base Number in mg KOH/g as measured by the method of ASTM D2896.

The term "hydrocarbyl" as employed herein refers to both straight and branched saturated, unsaturated, and/or substituted chain radicals of from 1 to 100 carbon atoms.

The term "alkyl" as employed herein refers to straight, branched, and/or substituted saturated chain radicals of from 1 to 100 carbon atoms.

The term "alkenyl" as employed herein refers to straight, branched, and/or substituted unsaturated chain radicals of from 3 to 10 carbon atoms.

The Phenolic Dimer

The novel phenolic dimers of the present invention are represented by Formula I:

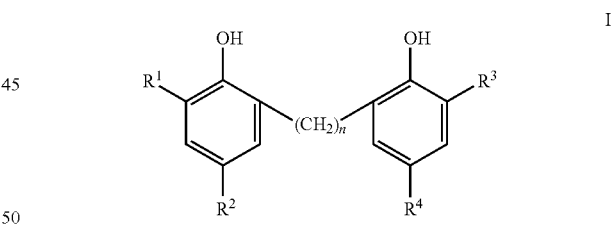

wherein in Formula I, $R^1$ and $R^3$ independently represent an alkyl or alkenyl group; $R^2$ and $R^4$ independently represent a hydrocarbyl group; and n is 1-3, with the proviso that each of $R^2$ and $R^4$ is not tert-dodecyl when each of $R^1$ and $R^3$ is methyl and n is 1.

Each $R^1$ and $R^3$ may be the same as the other, although they may be different. In one embodiment, $R^1$ and $R^3$ are independently alkyl groups containing 1 to 6 carbon atoms. In another embodiment, $R^1$ and $R^3$ are independently alkenyl groups containing 3 to 5 carbon atoms. Examples of useful $R^1$ and $R^3$ groups are methyl, ethyl, propyl, n-butyl, isobutyl, 1-propenyl, 1-butenyl, and 2-butenyl.

In other embodiments, each $R^1$ and $R^3$ is the same alkyl group having the same number of carbon atoms as described above. In another embodiment, each $R^1$ and $R^3$ is methyl.

Each $R^2$ and $R^4$ may be the same as the other, although they may be different. In one embodiment, $R^2$ and $R^4$ are independently hydrocarbyl groups containing 10 to 100 carbon atoms.

In another embodiment, $R^2$ and $R^4$ are independently alkyl groups containing 10 to 100 carbon atoms. In yet another embodiment, $R^2$ and $R^4$ are independently alkyl groups containing 12 to 75 carbon atoms. In still yet another embodiment, $R^2$ and $R^4$ are independently alkyl groups containing 25 to 75 carbon atoms. In another embodiment, $R^2$ and $R^4$ are independently alkyl groups containing 55 to 75 carbon atoms. In yet another embodiment, $R^2$ and $R^4$ are independently alkyl groups containing 35 to 45 carbon atoms. Examples of useful $R^2$ and $R^4$ groups are dodecyl and polyisobutyl.

In other embodiments, each $R^2$ and $R^4$ is the same alkyl group having the same number of carbon atoms as described above.

A useful phenolic dimer is represented by Formula I wherein $R^1$ is methyl, $R^2$ is polyisobutyl, $R^3$ is methyl, $R^4$ is polyisobutyl, and n is 1. Another useful phenolic dimer is represented by Formula I wherein $R^1$ is methyl, $R^2$ is polyisobutyl containing 10 to 100 carbon atoms, $R^3$ is methyl, $R^4$ is polyisobutyl containing 10 to 100 carbon atoms, and n is 1. Still yet another useful phenolic dimer is represented by Formula I wherein $R^1$ is methyl, $R^2$ is polyisobutyl containing 12 to 75 carbon atoms, $R^3$ is methyl, $R^4$ is polyisobutyl containing 12 to 75 carbon atoms, and n is 1. Another useful phenolic dimer is represented by Formula I wherein $R^1$ is methyl, $R^2$ is polyisobutyl containing 25 to 75 carbon atoms, $R^3$ is methyl, $R^4$ is polyisobutyl containing 25 to 75 carbon atoms, and n is 1. Still yet another useful phenolic dimer is represented by Formula I wherein $R^1$ is methyl, $R^2$ is polyisobutyl containing 55 to 75 carbon atoms, $R^3$ is methyl, $R^4$ is polyisobutyl containing 55 to 75 carbon atoms, and n is 1. Another useful phenolic dimer is represented by Formula I wherein $R^1$ is methyl, $R^2$ is polyisobutyl containing 35 to 45 carbon atoms, $R^3$ is methyl, $R^4$ is polyisobutyl containing 35 to 45 carbon atoms, and n is 1. A further useful phenolic dimer is represented by Formula I wherein $R^1$ is methyl, $R^2$ is dodecyl, $R^3$ is methyl, $R^4$ is dodecyl, and n is 1.

The novel phenolic dimers of Formula I can, in one embodiment, be prepared by contacting or reacting formaldehyde, in the presence of a catalyst, with a compound of Formula II:

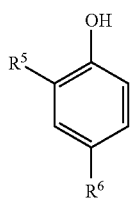

II wherein in Formula II, $R^5$ represents an alkyl or alkenyl group and $R^6$ represents a hydrocarbyl group.

In one embodiment, $R^5$ is an alkyl group containing 1 to 6 carbon atoms. Examples of useful $R^5$ groups are methyl, ethyl, propyl, n-butyl, isobutyl, 1-propenyl, 1-butenyl, and 2-butenyl. In another embodiment, $R^5$ is methyl.

In one embodiment, $R^6$ is a hydrocarbyl group containing 10 to 100 carbon atoms.

In another embodiment, $R^6$ is an alkyl group containing 10 to 100 carbon atoms. In yet another embodiment, $R^6$ is an alkyl group containing 12 to 75 carbon atoms. In still yet another embodiment, $R^6$ is an alkyl group containing 25 to 75 carbon atoms. In another embodiment, $R^6$ is an alkyl group containing 55 to 75 carbon atoms. In yet another embodiment, $R^6$ is an alkyl group containing 35 to 45 carbon atoms. Examples of useful $R^6$ groups are dodecyl and polyisobutyl.

A useful starting monomeric compound is represented by Formula II wherein $R^5$ is methyl and $R^6$ is polyisobutyl. Another useful starting monomeric compound is represented by Formula II wherein $R^5$ is methyl and R6 is polyisobutyl containing 10 to 100 carbon atoms. Still yet another useful starting monomeric compound is represented by Formula II wherein $R^5$ is methyl and $R^6$ is polyisobutyl containing 12 to 75 carbon atoms. Another useful starting monomeric compound is represented by Formula II wherein $R^5$ is methyl and $R^6$ is polyisobutyl containing 25 to 75 carbon atoms. Still yet another useful starting monomeric compound is represented by Formula II wherein $R_5$ is methyl and $R^6$ is polyisobutyl containing 55 to 75 carbon atoms. Another useful starting monomeric compound is represented by Formula II wherein $R^5$ is methyl and $R^6$ is polyisobutyl containing 35 to 45 carbon atoms. A further useful starting monomeric compound is represented by Formula II wherein $R^5$ is methyl and $R^6$ is dodecyl.

Suitable catalysts include, but are not limited to, any amine-containing catalyst or an acid. Examples of useful catalysts include 3-(dimethylamino)propylamine, ethylenediamine, and sulfuric acid. In one embodiment, the catalyst is 3-(dimethylamino)propylamine.

The amount of catalyst added to the dimerization reaction mixture is sufficient to provide about 0.2 to about 2%, by weight, based upon the weights of all components added to the dimerization reaction mixture. A useful amount of catalyst is about 0.5 to about 1%, by weight, based upon the weights of all components added to the dimerization reaction mixture.

In one embodiment, the amount of formaldehyde added to the dimerization reaction mixture is sufficient to provide about 1 to about 5%, by weight, based upon the weights of all components added to the dimerization reaction mixture. A useful amount of formaldehyde is about 1.2 to about 2%, by weight, based upon the weights of all components added to the dimerization reaction mixture.

The formaldehyde may be added to the dimerization reaction as a solid or in the form of a solution. A useful form of formaldehyde is a solution. In one embodiment, the formaldehyde is added to the dimerization reaction in the form of a 37% solution. In another embodiment, the formaldehyde is added to the dimerization reaction in the form of a 44% solution. The formaldehyde may be added to the initial reactants all at once, or part may be added to the initial reactants with the remainder being added in one or more portions at a subsequent stage or stages in the process.

The remainder of the dimerization reaction mixture consists of the monomeric compound represented by Formula II.

The isolated solution containing the novel phenolic dimer reaction product will contain no more than 1000 parts per million water. In one embodiment, the isolated solution containing the novel phenolic dimer reaction product will contain no more than 500 parts per million water.

The novel phenolic dimer reaction product is not a Mannich base.

The novel phenolic dimers of Formula I are useful as a friction modifier and can be used in lubricating oil compositions to provide anti-wear benefit. In one embodiment, the novel phenolic dimers of Formula I can be added to a base oil to yield a lubricating oil composition. In another embodiment, the novel phenolic dimers of Formula I can be added to, or used in, a lubricating oil concentrate.

The Overbased Phenolic Dimer

The novel, overbased compound of the invention is a compound, or a salt form thereof, represented by Formula III:

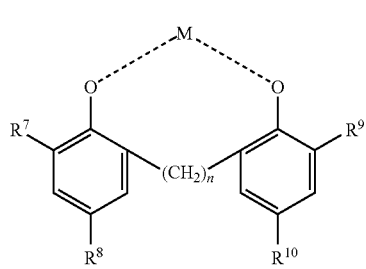

wherein in Formula III, $R^7$ and $R^9$ independently represent an alkyl or alkenyl group; $R^8$ and $R^{10}$ independently represent a hydrocarbyl group; M is an alkaline earth metal; and n is 1-3.

Each $R^7$ and $R^9$ may be the same as the other, although they may be different. In one embodiment, $R^7$ and $R^9$ are independently alkyl groups containing 1 to 6 carbon atoms. In another embodiment, $R^7$ and $R^9$ are independently alkenyl groups containing 3 to 5 carbon atoms. Examples of useful $R^7$ and $R^9$ groups are methyl, ethyl, propyl, n-butyl, isobutyl, 1-propenyl, 1-butenyl, and 2-butenyl.

In other embodiments, each $R^7$ and $R^9$ is the same alkyl group having the same number of carbon atoms as described above. In another embodiment, each $R^7$ and $R^9$ is methyl.

Each $R^8$ and $R^{10}$ may be the same as the other, although they may be different. In one embodiment, $R^8$ and $R^{10}$ are independently hydrocarbyl groups containing 10 to 100 carbon atoms.

In another embodiment, $R^8$ and $R^{10}$ are independently alkyl groups containing 10 to 100 carbon atoms. In yet another embodiment, $R^8$ and $R^{10}$ are independently alkyl groups containing 12 to 75 carbon atoms. In still yet another embodiment, $R^8$ and $R^{10}$ are independently alkyl groups containing 25 to 75 carbon atoms. In another embodiment, $R^8$ and $R^{10}$ are independently alkyl groups containing 55 to 75 carbon atoms. In yet another embodiment, $R^8$ and $R^{10}$ are independently alkyl groups containing 35 to 45 carbon atoms. Examples of useful $R^8$ and $R^{10}$ groups are dodecyl and polyisobutyl.

In other embodiments, each $R^8$ and $R^{10}$ is the same alkyl group having the same number of carbon atoms as described above.

M is, or comprises at least one, or a source of one, alkaline earth metal. Examples of M include calcium, magnesium, or barium, and mixtures, salts, or precursors thereof. The M can be provided in the form of calcium, magnesium, and/or barium salts or complexes, such as, but not limited to, oxides, hydroxides, halides, carbonates, or sulfonates.

A useful overbased compound is represented by Formula III wherein $R^7$ is methyl, $R^8$ is polyisobutyl, $R^9$ is methyl, $R^{10}$ is polyisobutyl, M is calcium, and n is 1. Another useful overbased compound is represented by Formula III wherein $R^7$ is methyl, $R^8$ is polyisobutyl containing 10 to 100 carbon atoms, $R^9$ is methyl, $R^{10}$ is polyisobutyl containing 10 to 100 carbon atoms, M is calcium, and n is 1. Still yet another useful overbased compound is represented by Formula III wherein $R^7$ is methyl, $R^8$ is polyisobutyl containing 12 to 75 carbon atoms, $R^9$ is methyl, $R^{10}$ is polyisobutyl containing 12 to 75 carbon atoms, M is calcium, and n is 1. Another useful overbased compound is represented by Formula III wherein $R^7$ is methyl, $R^8$ is polyisobutyl containing 25 to 75 carbon atoms, $R^9$ is methyl, $R^{10}$ is polyisobutyl containing 55 to 75 carbon atoms, M is calcium, and n is 1. Still yet another useful overbased compound is represented by Formula III wherein $R^7$ is methyl, $R^8$ is polyisobutyl containing 55 to 75 carbon atoms, $R^9$ is methyl, $R^{10}$ is polyisobutyl containing 55 to 75 carbon atoms, M is calcium, and n is 1. Another useful overbased compound is represented by Formula III wherein $R^7$ is methyl, $R^8$ is polyisobutyl containing 35 to 45 carbon atoms, $R^9$ is methyl, $R^{10}$ is polyisobutyl containing 35 to 45 carbon atoms, M is calcium, and n is 1. A further useful overbased compound is represented by Formula III wherein $R^7$ is methyl, $R^8$ is dodecyl, $R^9$ is methyl, $R^{10}$ is dodecyl, M is calcium, and n is 1.

One useful salt form of the overbased compounds of Formula III, as described above, is the calcium carbonate salt.

The overbased phenolic dimer of Formula III is prepared by contacting or reacting the novel phenolic dimer of Formula I with an alkaline earth metal source in the presence of carbon dioxide, a saturated or unsaturated carboxylic acid, a $C_1$-$C_{20}$ monohydric alcohol, a $C_2$-$C_4$ polyhydric alcohol, and optionally a base oil. The overbasing reaction is shown below in Schematic 1, wherein $R^1$, $R^2$, $R^3$, $R^4$, $R^7$, $R^8$, $R^9$, $R^{10}$, M, and n are as defined above and x is 0-5.

Schematic 1

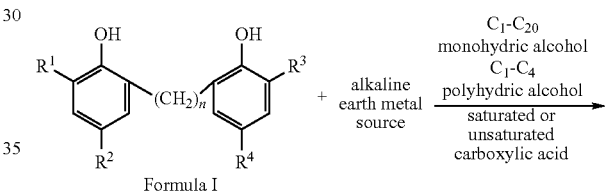

Additionally, herein is presented a product formed by this process.

The novel phenolic dimer of Formula I can be present in the overbasing reaction mixture in an amount of about 15 to about 50%, alternatively, about 17 to about 22%, by weight, based upon the weights of all components added to the overbasing reaction mixture.

The alkaline earth metal source may suitably be an alkaline earth metal oxide or hydroxide, with the hydroxide being particularly useful. One useful alkaline earth metal is calcium. The amount of alkaline earth metal source used in the overbasing reaction will depend on a number of factors, including the nature of the phenol or phenate and the amount of a base oil that can optionally be added to the reaction mixture. Typically, the weight ratio of the alkaline earth metal source to the novel phenolic dimer of Formula I used in the overbasing reaction is 0.1-1:1. A useful weight ratio of the alkaline earth metal source to the novel phenolic dimer of Formula I used in the overbasing reaction is 0.2-0.8:1. The alkaline earth metal source may be added to the initial reactants all at once, or part may be added to the initial reactants with the remainder being added in one or more portions at a subsequent stage or stages in the process.

Suitably, the alkaline earth metal source in the reactant mixture is present in one embodiment in an amount of about 5 to about 20%, by weight, based upon the weights of all components added to the overbasing reaction mixture. Another useful amount of alkaline earth metal source is about 7 to about 16%, by weight, based upon the weights of all components added to the overbasing reaction mixture.

The carbon dioxide can be added to the overbasing reaction in the form of a gas or a solid. A useful form of the carbon dioxide is a gas. When used in gaseous form, the carbon dioxide may suitably be blown through the overbasing reaction mixture at a flow rate of about 150 to about 300 cc/min for about 25 to about 90 minutes.

In one embodiment, a carboxylic acid can be added to the reaction mixture. If used, the amount of saturated or unsaturated carboxylic acid added to the reaction should be sufficient to provide up to about 20%, by weight, based upon the weights of all components added to the overbasing reaction mixture. A useful amount of carboxylic acid is about 2 to about 20%, by weight, based upon the weights of all components added to the reaction mixture. Another useful amount of carboxylic acid is about 5 to about 15%, by weight, based upon the weights of all components added to the reaction mixture.

Examples of suitable saturated carboxylic acids include capric acid, lauric acid, myristic acid, palmitic acid, stearic acid, isostearic acid, arachidic acid, behenic acid, and lignoceric acid. Examples of suitable unsaturated carboxylic acids include lauroleic acid, myristoleic acid, palmitoleic acid, oleic acid, gadoleic acid, erucic acid, ricinoleic acid, linoleic acid, and linolenic acid. Mixtures of acids may also be employed, such as rape top fatty acids. Particularly suitable mixtures of acids are those commercial grades containing a range of acids, including both saturated and unsaturated acids. Such mixtures may be obtained synthetically or may be derived from natural products, such as cotton oil, ground nut oil, coconut oil, linseed oil, palm kernel oil, olive oil, corn oil, palm oil, castor oil, soyabean oil, sunflower oil, herring oil, sardine oil, and tallow. Instead of, or in addition to, the carboxylic acid, there may be used an ester of acid anhydride, of the acid, preferably the acid anhydride. In one embodiment, where a salt of the carboxylic acid is used, the salt is an alkaline earth metal salt. In another embodiment, a carboxylic acid or a mixture of carboxylic acids is used. An example of a carboxylic acid that is useful is oleic acid.

The $C_1$-$C_{20}$ monohydric alcohol, if present, can be used in an amount sufficient to provide up to about 30%, by weight, based upon the weights of all components added to the overbasing reaction mixture. Another amount of the $C_1$-$C_{20}$ monohydric alcohol is about 2 to about 20%, by weight, based upon the weights of all components added to the overbasing reaction mixture. A useful amount of the $C_1$-$C_{20}$ monohydric alcohol is about 4 to about 10%, by weight, based upon the weights of all components added to the overbasing reaction mixture. Examples of the $C_1$-$C_{20}$ monohydric alcohol include methanol, 2-ethylhexanol, cyclohexanol, and benzyl alcohol. A useful $C_1$-$C_{20}$ monohydric alcohol is 2-ethylhexanol.

The $C_2$-$C_4$ polyhydric alcohol, if used, can be present in an amount sufficient to provide about 1 to about 10%, by weight, based upon the weights of all components added to the overbasing reaction mixture. A useful amount of $C_2$-$C_4$ polyhydric alcohol is about 1.5 to about 6%, by weight, based upon the weights of all components added to the overbasing reaction mixture. An example of a suitable $C_2$-$C_4$ polyhydric alcohol is a dihydric alcohol, such as ethylene glycol or propylene glycol. Another example of a suitable $C_2$-$C_4$ polyhydric alcohol is a trihydric alcohol, such as glycerol. A useful $C_2$-$C_4$ polyhydric alcohol is ethylene glycol.

In one embodiment, the overbasing reaction occurs in the presence of a base oil to yield a lubricating oil composition.

Base Oil

The base oil used in the lubricating oil compositions herein may be selected from any of the base oils in Groups I-V as specified in the American Petroleum Institute (API) Base Oil Interchangeability Guidelines. The five base oil groups are as follows:

| Base oil Category | Sulfur (%) | | Saturates (%) | Viscosity Index |
|---|---|---|---|---|
| Group I | >0.03 | and/or | <90 | 80 to 120 |
| Group II | ≦0.03 | and | ≧90 | 80 to 120 |
| Group III | ≦0.03 | and | ≧90 | ≧120 |
| Group IV | All polyalphaolefins (PAOs) | | | |
| Group V | All others not included in Groups I, II, III, or IV | | | |

Groups I, II and III are mineral oil process stocks.

The base oil used in the inventive lubricating oil composition may be a natural oil, synthetic oil or mixture thereof. The natural oils that are useful include animal oils and vegetable oils, such as castor oil, lard oil, olive oil, peanut oil, corn oil, soybean oil, and linseed oil, as well as mineral lubricating oils, such as liquid petroleum oils and solvent-treated or acid-treated mineral lubricating oils of the paraffinic, naphthenic or mixed paraffinic-naphthenic types. Such oils may be partially or fully hydrogenated, if desired. Oils derived from coal or shale are also useful.

The amount of base oil that can optionally be added to the overbasing reaction should be sufficient to provide about 20 to about 80%, by weight, based upon the weights of all components added to the overbasing reaction mixture. A useful amount of base oil is about 40 to about 70%, by weight, based upon the weights of all components added to the overbasing reaction mixture.

Useful lubricating oil compositions herein may have a viscosity of up to about 525 cSt at 100° C., and in one embodiment about 20 to about 200 cSt at 100° C., and in another embodiment about 20 to about 120 cSt at 100° C.

The TBN of the lubricating oil compositions described herein can be about 50 to about 500. A useful TBN of the lubricating oil compositions described herein can be about 100 to about 400.

In addition to either the novel phenolic dimer or the novel overbased phenolic dimer described herein, the lubricating oil composition may also contain other additives well-known in the art, such as polymeric viscosity modifiers, detergents, antioxidants, dispersants, rust inhibitors, antiwear agents, boron-containing compounds, friction modifiers, pour-point depressants, and antifoaming agents.

The lubricating oil compositions herein also can optionally contain one or more polymeric viscosity modifier. Polymeric viscosity modifiers reduce the rate of change of viscosity with temperature, i.e. they cause minimal increase in engine oil viscosity at low temperature but considerable increase at high temperature. The polymeric viscosity modifier, if present, can be used in an amount sufficient to provide up to about 12%, by weight, based upon the final weight of the lubricating oil composition. Another amount of the polymeric viscosity modifier that can be used is about 0.5 to about 10%, by weight, based upon the final weight of the lubricating oil composition.

Examples of polymeric viscosity modifiers include polyolefins, polyisobutylenes, polymethacrylates, ethylene/propylene copolymers, polyacrylates, styrene/maleic ester copolymers, olefin copolymers, and hydrogenated styrene/butadiene copolymers. A useful polymeric viscosity modifier is a dispersant olefin copolymer.

The lubricating oil compositions herein also can optionally contain one or more detergents. The detergent, if present, can be used in an amount sufficient to provide up to about 10%, by weight, based upon the final weight of the lubricating oil composition. Another amount of the detergent that can be used is about 0.02 to about 2.5%, by weight, based upon the final weight of the lubricating oil composition.

Examples of detergents include metallic additives containing charged polar groups, such as sulfonates, phenates, carboxylates, salicylates, or phosphonates, with aliphatic, cycloaliphatic, or alkylaromatic chains, and several metal ions that will include at least one alkaline earth metal ion. These detergents function by lifting deposits in the combustion chamber, which can include related injection valves, injection ports, and so forth. The alkaline earth metal-containing detergent compound includes calcium, magnesium, barium and strontium salts imparting detergent action in a fuel-oil composition. Examples include neutral and overbased alkaline earth metal sulphonates, neutral and overbased alkaline earth metal salicylates, and neutral and overbased alkaline earth metal phenates. These detergents may include alkaline earth metal salts of petroleum sulphonic acids and long chain mono- or di-alkylarylsulphonic acids with each alkyl group comprising 12-18 carbon atoms and the aryl group being benzyl, tolyl, and xylyl. These detergents also may include alkaline earth metal phenates of alkylphenols and alkylmercaptophenols in which the linear or branched alkyl groups comprising from 4-50 carbon atoms and more particularly from 8-20 carbon atoms. Specific examples of the detergent include salts such as selected from the group consisting of neutral calcium sulphonate, neutral $C_{14}$-$C_{24}$ alphaolefin calcium sulfonate, overbased calcium sulphonate, overbased $C_{14}$-$C_{24}$ alphaolefin calcium sulfonate, neutral calcium phenate, overbased calcium phenate, neutral calcium salicylate, overbased calcium salicylate, neutral magnesium sulphonate, overbased magnesium sulphonate, neutral magnesium phenate, overbased magnesium phenate, neutral magnesium salicylate, overbased magnesium salicylate, or combinations and mixtures thereof.

Useful detergents are neutral calcium sulfonate, overbased calcium sulfonate, neutral calcium salicylate, overbased calcium salicylate, neutral calcium phenate, and overbased calcium phenate. In one embodiment, the neutral calcium sulfonate is a $C_{14}$-$C_{24}$ alphaolefin calcium sulfonate. In another embodiment, the overbased calcium sulfonate is a $C_{14}$-$C_{24}$ alphaolefin calcium sulfonate. In yet another embodiment, the detergent is a mixture of overbased $C_{14}$-$C_{24}$ alphaolefin calcium sulfonate and neutral $C_{14}$-$C_{24}$ alphaolefin calcium sulfonate, wherein each detergent is present in an amount sufficient to provide up to about 5%, by weight, based upon the final weight of the lubricating oil composition. In still yet another embodiment, the detergent is a mixture of about 0.01 to about 1% overbased $C_{14}$-$C_{24}$ alphaolefin calcium sulfonate and about 0.1 to about 2% neutral $C_{14}$-$C_{24}$ alphaolefin calcium sulfonate, by weight, based upon the final weight of the lubricating oil composition.

The lubricating oil compositions herein also can optionally contain one or more antioxidants. The antioxidant, if present, can be used in an amount sufficient to provide up to about 10% by weight, based upon the final weight of the lubricating oil composition. Another amount of the antioxidant that can be used is about 0.1 to about 4%.

Examples of antioxidants for use in lubricating oil compositions are well known and include a variety of chemical types including phenates, phenate sulfides, sulfurized olefins, phosphosulfurised terpenes, sulfurised esters, aromatic amines, phenols, and hindered phenols. Useful antioxidants include diarylamines and high molecular weight phenols. In one embodiment, the lubricating oil composition contains a mixture of a diarylamine and a high molecular weight phenol, such that each antioxidant is present in an amount sufficient to provide up to about 5%, by weight, based upon the final weight of the lubricating oil composition. In another embodiment, the antioxidant is a mixture of about 0.3 to about 1.5% diarylamine and about 0.4 to about 2.5% high molecular weight phenol, by weight, based upon the final weight of the lubricating oil composition.

The lubricating oil compositions herein also can optionally contain one or more dispersants. The dispersant, if present, can be used in an amount sufficient to provide up to about 12%, by weight, based upon the final weight of the lubricating oil composition. Another amount of the dispersant that can be used is about 3 to about 10%, by weight, based upon the final weight of the lubricating oil composition. In one embodiment, the lubricating oil composition utilizes a mixed dispersant system.

Dispersants used in lubricating oil compositions include primarily what are sometimes referred to as "ashless" dispersants because, prior to mixing in a lubricating oil composition, the dispersants do not contain ash-forming metals and the dispersants do not normally contribute any ash forming metals when added to a lubricating oil compositions. Dispersants are characterized by a polar group attached to a relatively high molecular weight hydrocarbon chain.

One class of dispersants is Mannich bases. Mannich bases are materials that are formed by the condensation of a higher molecular weight, alkyl substituted phenol, an alkylene polyamine, and an aldehyde such as formaldehyde. Mannich bases are described in more detail in U.S. Pat. No. 3,634,515.

Another class of dispersants is succinimide compounds. These materials are formed by the reaction of a hydrocarbyl-substituted succinic acylating agent and an amine. A more detailed description of succinimide compounds suitable for the lubricating oil compositions described herein is described in European Patent No. 976 814 and U.S. Pat. No. 4,234,435.

A third class of dispersants is high molecular weight esters. This class of dispersants is described in more detail in U.S. Pat. No. 3,381,022.

Other dispersants include polymeric dispersant additives, which are generally hydrocarbon-based polymers that contain polar functionality to impart dispersancy characteristics to the polymer.

A useful class of dispersants is the carboxylic dispersants. Carboxylic dispersants include succinic-based dispersants, which are the reaction product of a hydrocarbyl substituted succinic acylating agent with an organic hydroxy compound or, preferably, an amine containing at least one hydrogen attached to a nitrogen atom, or a mixture of said hydroxy compound and amine. The term "succinic acylating agent" refers to a hydrocarbon-substituted succinic acid or succinic acid-producing compound. Examples of succinic acylating agents include hydrocarbyl-substituted succinic acids, anhydrides, esters (including half esters) and halides.

A useful dispersant is a glycolated capped succinimide.

The lubricating oil compositions herein may also optionally contain one or more rust inhibitors. The rust inhibitor, if present, can be used in an amount sufficient to provide up to about 5%, by weight, based upon the final weight of the lubricating oil composition.

The rust inhibitor may be a single compound or a mixture of compounds having the property of inhibiting corrosion of ferrous metal surfaces. Non-limiting examples of rust inhibitors useful herein include oil-soluble high molecular weight organic acids, such as 2-ethylhexanoic acid, lauric acid, myristic acid, palmitic acid, oleic acid, linoleic acid, linolenic acid, behenic acid, and cerotic acid, as well as oil-soluble polycarboxylic acids including dimer and trimer acids, such as those produced from tall oil fatty acids, oleic acid, and linoleic acid. Other suitable corrosion inhibitors include long-chain alpha, omega-dicarboxylic acids in the molecular weight range of 600 to 3000 and alkenylsuccinic acids in which the alkenyl group contains 10 or more carbon atoms such as, tetrapropenylsuccinic acid, tetradecenylsuccinic acid, and hexadecenylsuccinic acid. Another useful type of acidic corrosion inhibitors are the half esters of alkenyl succinic acids having 8 to 24 carbon atoms in the alkenyl group with alcohols such as the polyglycols. The corresponding half amides of such alkenyl succinic acids are also useful. A useful rust inhibitor is a high molecular weight organic acid.

The lubricating oil compositions herein may optionally contain one or more antiwear agents. The antiwear agent, if present, can be used in an amount sufficient to provide up to about 5%, by weight, based upon the final weight of the lubricating oil composition. Another amount of the antiwear agent that can be used is about 0.1 to about 5%, by weight, based upon the final weight of the lubricating oil composition.

Examples of antiwear agents include, but are not limited to, a metal thiophosphate, especially a zinc dialkyldithiophosphate, a phosphoric acid ester or salt thereof, a phosphite, and a phosphorus-containing carboxylic ester, ether, or amide. The phosphorus containing antiwear agents are more fully described in European Patent 612 839. A useful antiwear agent is zinc dialkylthiophosphate.

The lubricating oil compositions herein may optionally contain one or more boron-containing compounds. The boron-containing compound, if present, can be used in an amount sufficient to provide up to about 8%, by weight, based upon the final weight of the lubricating oil composition. Another amount of the boron-containing compound that can be used is about 0.5 to about 7%, by weight, based upon the final weight of the lubricating oil composition.

Examples of boron-containing compounds include borate esters, borated fatty amines, borated epoxides, and borated dispersants, such as borated succinimide dispersants, as disclosed in U.S. Pat. No. 5,883,057, columns 29-33. A useful boron-containing compound is a borated polyisobutylene succinimide dispersant that may optionally be capped with maleate.

The lubricating oil compositions herein may optionally contain one or more friction modifiers. The friction modifier, if present, can be used in an amount sufficient to provide up to about 5%, by weight, based upon the final weight of the lubricating oil composition. Another amount of the friction modifier that can be used is about 0.05 to about 1%, by weight, based upon the final weight of the lubricating oil composition.

Examples of friction modifiers include fatty amines, esters, especially glycerol esters such as glycerol monooleate, borated glycerol esters, fatty phosphites, fatty acid amides, fatty epoxides, borated fatty epoxides, alkoxylated fatty amines, borated alkoxylated fatty amines, metal salts of fatty acids, sulfurized olefins, fatty imidazolines, condensation products of carboxylic acids and polyalkylene-polyamines, amine salts of alkylphosphoric acids, and molybdenum-containing antioxidants or friction modifiers such as, but not limited to molybdenum dithiocarbamates, molybdenum amides, and molybdenum carboxylates. Among suitable molybdenum friction modifiers are molybdenum and sulfur-containing compositions derived from a molybdenum compound, a basic nitrogen-containing compound, and carbon disulfide. The basic nitrogen compound can be a hydrocarbyl amine or a reaction product of a carboxylic acid with an alkylene polyamine. The molybdenum compound can be an acidic molybdenum compound such as molybdic acid. Molybdenum-containing sulfur-free compounds are also useful herein. A useful friction modifier is glycerol monooleate.

The lubricating oil compositions herein may optionally contain one or more pour point depressants. The pour point depressant, if present, can be used in an amount sufficient to provide up to about 1%, by weight, based upon the final weight of the lubricating oil composition. Another amount of the pour point depressant that can be used is about 0.04 to about 0.5%, by weight, based upon the final weight of the lubricating oil composition. A useful pour point depressant is polymethylmethacrylate.

The lubricating oil compositions herein may optionally contain one or more antifoaming agents. The antifoaming agent, if present, can be used in an amount sufficient to provide up to about 1%, by weight, based upon the final weight of the lubricating oil composition. Another amount of the antifoaming agent that can be used is about 0.001 to about 0.015%, by weight, based upon the final weight of the lubricating oil composition. A useful antifoaming agent is a siloxane.

The TBN of the lubricating oil compositions containing the optional additives, described herein, can be about 2 to about 20. A useful TBN of the lubricating oil compositions containing the optional additives described herein can be about 5 to about 12.

In one embodiment, the final lubricating oil composition contains up to about 5% novel overbased dimer, up to about 12% polymeric viscosity modifier, up to about 10% detergent, up to about 10% antioxidant, up to about 12% dispersant, up to about 5% rust inhibitor, up to about 5% antiwear agent, up to about 8% boron-containing compound, up to about 5% friction modifier, up to about 1% pour point depressant, and up to about 1% antifoaming agent.

In another embodiment, the final lubricating oil composition contains about 2 to about 4.5% novel overbased dimer, about 0.5 to about 10% polymeric viscosity modifier, about 0.02 to about 2.5% detergent, about 0.1 to about 4% antioxidant, about 3 to about 10% dispersant, about 0.1 to about 5% antiwear agent, about 0.5 to about 7% boron-containing compound, about 0.05 to about 1% friction modifier, about 0.04 to about 0.5% pour point depressant, and about 0.001 to about 0.015% antifoaming agent.

In still another embodiment, the final lubricating oil composition contains up to about 5% novel overbased dimer, up to about 12% dispersant olefin copolymer, up to about 5% neutral calcium sulfonate, up to about 5% overbased calcium sulfonate, up to about 5% diarylamine, up to about 5% high molecular weight phenol, up to about 12% glycolated capped succinimide, up to about 5% zinc dialkyldithiophosphate, up to about 8% borated polyisobutylene succinimide, optionally capped with maleate, up to about 5% glycerol monooleate, up to about 1% pour point depressant, and up to about 1% antifoaming agent.

In yet another embodiment, the final lubricating oil composition contains about 2 to about 4.5% novel overbased dimer, about 0.5 to about 10% dispersant olefin copolymer, about 0.01 to about 1% overbased $C_{14}$-$C_{24}$ alphaolefin calcium sulfonate, about 0.1 to about 2% neutral $C_{14}$-$C_{24}$ alphaolefin calcium sulfonate, about 0.3 to about 1.5% diarylamine, about 0.4 to about 2.5% high molecular weight phenol, about 3 to about 10% glycolated capped succinimide, about 0.1 to about 5% zinc dialkyldithiophosphate, about 0.5 to about 7% borated polyisobutylene succinimide, about 0.05 to about 1% glycerol monooleate, about 0.04 to about 0.5% pour point depressant, and about 0.001 to about 0.015% antifoaming agent.

In still yet another embodiment, the final lubricating oil composition contains up to about 5% novel overbased dimer, up to about 12% dispersant olefin copolymer, up to about 5% neutral calcium salicylate, up to about 5% overbased calcium salicylate, up to about 5% diarylamine, up to about 5% high molecular weight phenol, up to about 12% glycolated capped succinimide, up to about 5% zinc dialkyldithiophospahte, up to about 8% borated polyisobutylene succinimide, optionally capped with maleate, up to about 5% glycerol monooleate, up to about 1% pour point depressant, and up to about 1% antifoaming agent.

In another embodiment, the final lubricating oil composition contains up to about 5% novel overbased dimer, up to about 12% dispersant olefin copolymer, up to about 5% neutral calcium phenate, up to about 5% overbased calcium phenate, up to about 5% diarylamine, up to about 5% high molecular weight phenol, up to about 12% glycolated capped succinimide, up to about 5% zinc dialkyldithiophospahte, up to about 8% borated polyisobutylene succinimide, optionally capped with maleate, up to about 5% glycerol monooleate, up to about 1% pour point depressant, and up to about 1% antifoaming agent.

The percentages of each component above represent the weight percent of each component, based upon the weight of the final lubricating oil composition. The remainder of the lubricating oil composition consists of a base oil.

The lubricating oil compositions presented herein have about 0.2 to about 1.8% sulfated ash (ASTM D874) and about 0.03 to about 0.18%, by weight, elemental phosphorous.

The lubricating oil compositions presented herein are particularly effective as engine lubricating oils having enhanced antiwear properties. These lubricating oil compositions are effective in a variety of applications, including crankcase lubricating oil compositions for spark-ignited and compression-ignited internal combustion engines, such as automobile and truck engines, two-cycle engines, aviation piston engines, marine engines, low-load diesel engines, and heavy duty diesel engines. The lubricating oil compositions will also find utility in applications including transmission fluids, such as transmission fluids for automatic, manual, and continuously variable transmissions, as well as in metal-working fluids.

The foregoing novel phenolic dimers and novel overbased phenolic dimers can be added directly to the base oil to form the lubricating oil composition. In one embodiment, however, the novel phenolic dimers, the novel overbased phenolic dimers and, optionally, one of the other additives described above, are diluted with a substantially inert, normally liquid organic diluent such as mineral oil, synthetic oil, naphtha, alkylated (e.g., $C_{10}$-$C_{13}$ alkyl) benzene, toluene or xylene to form a lubricating oil concentrate. These lubricating oil concentrates usually contain from about 1% to about 99% by weight, and in one embodiment 10% to 90% by weight of the diluent. The lubricating oil concentrates may be added to the base oil to form the lubricating oil composition.

The following examples are illustrative, but not limiting, of the methods and compositions of the present invention. Other suitable modifications and adaptations of the variety of conditions and parameters normally encountered in the field, and which are obvious to those skilled in the art, are within the spirit and scope of the invention. All patents and publications cited herein are fully incorporated by reference herein in their entirety.

EXAMPLE 1

Preparation of 4-Polyisobutyl Cresol Dimer 4-polyisobutyl cresol (1200 g) was placed in a 1 L 3-neck round bottom flask equipped with agitator, temperature controller, Dean-Stark trap and condenser as reactor. Nitrogen blanketing was utilized. The 4-polyisobutyl cresol was heated at 35-40° C. 3-(dimethylamino)propylamine (12 g) was added to the 4-polyisobutyl cresol. A 37% formaldehyde solution (96 g) was added over a 5-10 minute period, via addition funnel subsurface. The temperature of the reaction was maintained at a temperature lower than 60° C. The mixture was agitated for 15 minutes at 60° C. The mixture was then distilled at 150° C., under nitrogen sparging at 1.0 SCFM. The water was collected for 1.0 hour at 150 ° C. The remaining reaction mixture was cooled to about 80° C. Finally, the remaining reaction mixture was filtered through 11 cm filter paper and a pre-coat (15 g). The viscosity of the 4-polyisobutyl cresol dimer solution was 994 cSt. at 100° C.

EXAMPLE 2

Preparation of Overbased 4-Polyisobutyl Cresol Dimer 4-polyisobutyl cresol dimer (70 g) was placed in a 1 L 3-neck resin flask with bottom outlet equipped with agitator, addition funnel, thermometer, temperature controller, and condenser as reaction. Base oil (200 g) was then added. The mixture was agitated at 500±50 rpm. 2-ethylhexanol (40 g), ethylene glycol (5 g), oleic acid (50 g), and calcium hydroxide (42 g) were added to the mixture. The mixture was then agitated under a vacuum (11" Hg) and heated to 105° C. The vacuum pressure was then increased to 28.8" Hg. The mixture was allowed to react for 40 minutes under the vacuum. Then, the vacuum pressure was decreased to 11" Hg and the temperature was increased to 130° C. The vacuum was then released and more ethylene glycol (18 g) was added, drop by drop, over a 5 minute period, via addition funnel. Carbon dioxide was added as a gas subsurface at 130° C., for 40 minutes, at a rate of 260 cc/min. The temperature was again increased, to a temperature of 180° C., and the vacuum pressure was increased to 29: Hg. Then, the temperature was increased to 210° C. The mixture was maintained at a temperature of 210° C., and a vacuum pressure of 29" Hg, for one hour. Finally, the hot product was filtered using an 8% body aid and a pre-coat (15 g).

The TBN of the resulting lubricating composition was 164. The % calcium, by weight, was 5.72%. The viscosity of the resulting lubricating at 100° C. was 30.2 cSt.

EXAMPLE 3

Preparation of Overbased 4-Polyisobutyl Cresol Dimer

The procedure of Example 2 was followed, except that 100 g calcium hydroxide and 200 g polyisobutyl cresol dimer were used in the reaction.

The TBN of the resulting lubricating composition was 197. The % calcium, by weight, was 6.13%. The viscosity of the resulting lubricating composition at 100° C. was 118 cSt.

EXAMPLE 4

The procedure of Example 2 was followed using the specified amounts of the different components of the reaction. The TBN, % calcium, by weight, and viscosity of each resulting lubricating composition is shown in Table I.

EXAMPLE 5

A lubricating oil composition containing dispersant olefin copolymer (approximately 2%), borated polyisobutylene succinimide, capped with maleate, (3.3%), glycolated capped succinimide dispersant (1.4%), zinc dialkyldithiophosphate (1%), the novel overbased phenolic dimer (2.5%), neutral $C_{14}$-$C_{24}$ alphaolefin calcium sulfonate (0.48%), overbased $C_{14}$-$C_{24}$ alphaolefin calcium sulfonate (0.11%), diarylamine (0.7%), glycerol monooleate (0.4%), high molecular weight phenol (1.5%) was utilized in a Caterpillar heavy duty engine crankcase. The percentages of each component included in parentheses represent the weight percent of each component in the lubricating oil compositions, based upon the final weight of the lubricating oil composition. The remainder of the lubricating oil composition consists of Group II base oils.

This lubricating oil composition had a TBN of 8.3. The percentages of sulfated ash, sulfur, and phosphorous contained in the lubricating oil composition were 0.88%, 0.29%, and 0.107%, respectively.

The results from a CH-4 API Diesel Engine Performance test for the Caterpillar 1P engine utilizing the lubricating oil composition are described below.

The Weighted Demerits—1 P was 248.8, less than the maximum acceptable value of 350. The Top Groove Carbon was 31.8%, less than the maximum acceptable value of 36%. The Top Land Carbon was 24.8%, less than the maximum acceptable value of 40%. The Average Oil Consumption was 3.1 g/h, much less than the maximum acceptable value of 12.4 g/h. The Final Oil Consumption was 2.3 g/h, again, much less than the maximum acceptable value of 14.6 g/h.

Therefore, the lubricating oil composition described herein passed the CH-4 API Diesel Engine Performance test.

TABLE I

| Overbasing Polyisobutylcresol Dimer | | | | | | | | | | | | | |
|---|---|---|---|---|---|---|---|---|---|---|---|---|---|
| PAC | | 2-Ethy- | Ethylene Glycol | | Oleic | | | $CO_2$ | | | TBN | Visc @ | Filtration |
| Dimer (gm) | Bases Oil (gm) | hexanol (gm) | $1^{st}$ (gm) | $2^{nd}$ (gm) | Acid (gm) | Ca(OH)$_2$ (gm) | Time (min) | Flow Rate (cc/min) | (gm) | % Ca (%) | (mg KOH/g) | 100° (cST) | Rate |
| 200.0 | 200.0 | 40.0 | 5.0 | 18 | 50.0 | 50.0 | 80.0 | 270 | 42.4 | 4.53 | 125.0 | 66.9 | Poor |
| 200.0 | 200.0 | 40.0 | 5.0 | 18 | 50.0 | 50.0 | 80.0 | 270 | 42.4 | 4.01 | 116.0 | 66.8 | Ave. |
| 200.0 | 200.0 | 40.0 | 5.0 | 18 | 50.0 | 50.0 | 80.0 | 270 | 42.4 | 4.27 | 117.0 | 67.2 | Ave. |
| 200.0 | 200.0 | 40.0 | 5.0 | 18 | 50.0 | 50.0 | 80.0 | 270 | 42.4 | 3.18 | 83.7 | 58.6 | Ave. |
| 200.0 | 200.0 | 40.0 | 5.0 | 18 | 50.0 | 100.0 | 80.0 | 270 | 42.4 | 6.13 | 197.0 | 118.2 | Ave. |
| 200.0 | 200.0 | 40.0 | 5.0 | 18 | 50.0 | 50.0 | 53.0 | 270 | 28.1 | 5.07 | 138.0 | — | Ave. |
| 100.0 | 200.0 | 40.0 | 5.0 | 18 | 50.0 | 50.0 | 48.0 | 270 | 25.5 | — | 174.0 | 50.9 | Poor |
| 100.0 | 200.0 | 40.0 | 5.0 | 18 | 50.0 | 40.0 | 38.0 | 270 | 20.2 | 4.94 | 144.0 | 46.0 | Fast |
| 100.0 | 200.0 | 40.0 | 5.0 | 18 | 50.0 | 45.0 | 39.0 | 270 | 20.7 | 5.36 | 158.5 | 72.2 | Fast |
| 100.0 | 200.0 | 40.0 | 5.0 | 18 | 50.0 | 47.0 | 41.0 | 270 | 21.7 | 5.61 | 164.7 | 82.0 | Fast |
| 100.0 | 200.0 | 40.0 | 5.0 | 18 | 50.0 | 50.0 | 44.0 | 270 | 23.3 | 6.02 | 170.4 | 506.4 | Ave. |
| 100.0 | 200.0 | 20.0 | 2.5 | 9 | 52.1 | 47.0 | 32.0 | 270 | 17.0 | 4.37 | 121.8 | 39.4 | Ave. |
| 90.0 | 200.0 | 40.0 | 5.0 | 18 | 50.0 | 45.4 | 40.0 | 270 | 21.2 | 5.83 | 164.0 | 66.8 | Fast |
| 80.0 | 200.0 | 40.0 | 5.0 | 18 | 50.0 | 43.9 | 39.0 | 270 | 20.7 | — | 155.1 | 26.2 | Ave. |
| 90.0 | 200.0 | 40.0 | 5.0 | 18 | 50.0 | 45.4 | 43.0 | 270 | 22.8 | — | 160.5 | 39.0 | Poor |
| 90.0 | 200.0 | 40.0 | 5.0 | 18 | 50.0 | 45.4 | 40.0 | 270 | 21.2 | 5.61 | 164.4 | 35.6 | Poor |
| 90.0 | 200.0 | 40.0 | 5.0 | 18 | 50.0 | 45.4 | 40.0 | 270 | 21.2 | 5.64 | 153.4 | 36.5 | Poor |
| 90.0 | 200.0 | 40.0 | 5.0 | 18 | 50.0 | 45.4 | 54.6 | 212 | 22.7 | 5.59 | 158.1 | 40.6 | Poor |
| 70.0 | 200.0 | 40.0 | 5.0 | 18 | 50.0 | 42.3 | 40.5 | 270 | 21.5 | 5.94 | 163.1 | 28.9 | Good |
| 70.0 | 200.0 | 40.0 | 5.0 | 18 | 50.0 | 42.3 | 54.5 | 200 | 21.4 | 5.94 | 166.0 | 28.3 | Fast |
| 70.0 | 200.0 | 40.0 | 5.0 | 18 | 50.0 | 42.3 | 52.0 | 200 | 20.4 | 5.60 | 162.7 | 27.8 | Fast |
| 70.0 | 200.0 | 40.0 | 5.0 | 18 | 50.0 | 42.3 | 56.8 | 200 | 22.3 | 5.72 | 164.8 | 30.2 | Fast |

PAC = Polyisobutylcresol

What is claimed is:

1. A compound comprising Formula I:

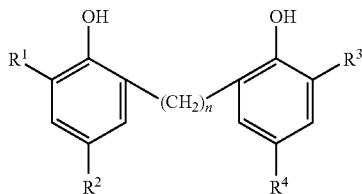

wherein:
$R^1$ and $R^3$ independently represent a methyl group;
$R^2$ and $R^4$ are each a polyisobutyl; and
n is 1-3; provided that each of $R^2$ and $R^4$ is not tert-dodecyl when each of $R^1$ and $R^3$ is methyl and n is 1.

2. The compound of claim 1, wherein each $R^2$ and $R^4$ is polyisobutyl containing 10 to 100 carbon atoms.

3. The compound of claim 1, wherein each $R^2$ and $R^4$ is polyisobutyl containing 55 to 75 carbon atoms.

4. The compound of claim 1, wherein n is 1.

5. The compound of claim 1, wherein $R^1$ and $R^3$ are each methyl; $R^2$ and $R^4$ are each polyisobutyl; and n is 1.

6. The compound of claim 5, wherein $R^1$ and $R^3$ is methyl; $R^2$ and $R^4$ are each polyisobutyl containing 10 to 100 carbon atoms; and n is 1.

7. A compound, or a salt form thereof, comprising Formula III:

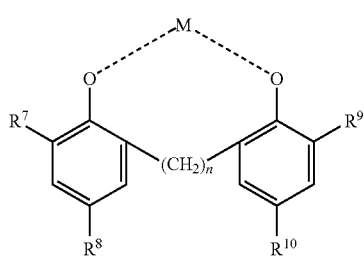

wherein:
$R^7$ and $R^9$ independently represent a methyl group;
$R^8$ and $R^{10}$ independently represent a hydrocarbyl group;
M is an alkaline earth metal; and
n is 1-3.

8. The compound of claim 7, wherein each $R^8$ and $R^{10}$ is polyisobutyl.

9. The compound of claim 8, wherein each $R^8$ and $R^{10}$ is polyisobutyl containing 10 to 100 carbon atoms.

10. The compound of claim 8, wherein each $R^8$ and $R^{10}$ is polyisobutyl containing 55 to 75 carbon atoms.

11. The compound of claim 7, wherein each $R^8$ and $R^{10}$ is dodecyl.

12. The compound of claim 7, wherein M is selected from a group consisting of calcium, magnesium, and barium.

13. The compound of claim 12, wherein M comprises calcium.

14. The compound of claim 7, wherein n is 1.

15. The compound of claim 7, wherein each $R^7$ and $R^9$ is methyl; each $R^8$ and $R^{10}$ is polyisobutyl; M is calcium; and n is 1.

16. The compound of claim 15, wherein each $R^7$ and $R^9$ is methyl; each $R^8$ and $R^{10}$ is polyisobutyl containing 10 to 100 carbon atoms; M is calcium; and n is 1.

17. The compound of claim 7, wherein the compound comprises the calcium carbonate salt form.

18. A process for preparing a compound of claim 7, said process comprising:
(a) contacting an alkaline earth metal source, a saturated or unsaturated carboxylic acid, a $C_1$-$C_{20}$ monohydric alcohol, and a $C_2$-$C_4$ polyhydric alcohol with a compound of Formula I

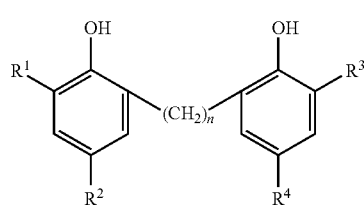

wherein, $R^1$, $R^2$, $R^3$, $R^4$, and n are as defined in claim 1; and
(b) adding carbon dioxide.

19. The process of claim 18, wherein the alkaline earth metal source is calcium hydroxide.

20. The process of claim 18, wherein the saturated or unsaturated carboxylic acid comprises oleic acid.

21. The process of claim 18, wherein the $C_1$-$C_{20}$ monohydric alcohol comprises 2-ethylhexanol.

22. The process of claim 18, wherein the $C_2$-$C_4$ polyhydric alcohol comprises ethylene glycol.

23. A lubricating oil composition comprising the overbased compound of claim 7.

24. A lubricating oil composition of claim 23, wherein said lubricating composition comprises one or more additional additives selected from the group consisting of a polymeric viscosity modifier, a detergent, an antioxidant, a dispersant, a rust inhibitor, an antiwear agent, a boron-containing compound, a friction modifier, a pour-point depressant, and an antifoaming agent.

25. The lubricating oil composition of claim 24, wherein said lubricating oil composition comprises up to about 12% polymeric viscosity modifier, up to about 10% detergent, up to about 10% antioxidant, up to about 12% dispersant, up to about 5% rust inhibitor, up to about 5% antiwear agent, up to about 8% boron-containing compound, up to about 5% friction modifier, up to about 1% pour point depressant, and up to about 1% antifoaming agent, wherein the percentage of each component represents the weight percent of each component based upon the weight of the final lubricating oil composition.

26. The lubricating oil composition of claim 25, wherein said lubricating oil composition comprises about 4 to about 10% polymeric viscosity modifier, about 0.1 to about 2.5% detergent, about 0.2 to about 4% antioxidant, about 4 to about 10% dispersant, about 0.25 to about 5% antiwear agent, about 1 to about 7% boron-containing compound, about 0.1 to about 1% friction modifier, about 0.1 to about 0.5% pour point depressant, and about 0.001 to about 0.015% antifoaming agent, wherein the percentage of each component represents the weight percent of each component based upon the weight of the final lubricating oil composition.

27. A lubricating oil composition prepared by a process comprising:
(a) combining the compound of claim 1, a base oil, an alkaline earth metal source, a saturated or unsaturated carboxylic acid, a $C_1$-$C_{20}$ monohydric alcohol, and a $C_2$-$C_4$ polyhydric alcohol; and (b) adding carbon dioxide.

28. The lubricating oil composition prepared by the process of claim 27, wherein the alkaline earth metal source comprises calcium hydroxide.

29. The lubricating oil composition prepared by the process of claim 27, wherein the saturated or unsaturated carboxylic acid comprises oleic acid.

30. The lubricating oil composition prepared by the process of claim 27, wherein the $C_1$-$C_{20}$ monohydric alcohol comprises 2-ethylhexanol.

31. The lubricating oil composition prepared by the process of claim 27, wherein the $C_2$-$C_4$ polyhydric alcohol comprises ethylene glycol.

32. A method for lubricating an internal combustion engine comprising adding the lubricating oil composition of claim 23 to said engine.

33. A method for lubricating transmissions comprising adding the lubricating oil composition of claim 23 to said transmission.

34. A method for lubricating a transmission according to claim 33 wherein said transmission is selected from a group consisting of a manual transmission, an automatic transmission, and a continuously variable transmission.

35. A lubricating oil concentrate comprising the overbased compound of claim 7.

36. A lubricating oil concentrate comprising the overbased compound of claim 7 in a substantially inert liquid organic diluent.

37. A lubricating oil concentrate of claim 35, wherein said lubricating concentrate comprises one or more additional additives selected from the group consisting of a polymeric viscosity modifier, a detergent, an antioxidant, a dispersant, a rust inhibitor, an antiwear agent, a boron-containing compound, a friction modifier, a pour-point depressant, and an antifoaming agent.

* * * * *